United States Patent
Ector, Jr. et al.

(10) Patent No.: US 6,817,192 B2
(45) Date of Patent: Nov. 16, 2004

(54) DEVICE TO RECORD AGE OF FOOD

(76) Inventors: Ralph A. Ector, Jr., 8 S. White St., Athens, TN (US) 37303; Lisa Ector, 8 S. White St., Athens, TN (US) 37303

(*) Notice: Subject to any disclaimer, the term of this patent is extended or adjusted under 35 U.S.C. 154(b) by 0 days.

(21) Appl. No.: 10/114,997

(22) Filed: Apr. 4, 2002

(65) Prior Publication Data

US 2002/0154574 A1 Oct. 24, 2002

Related U.S. Application Data

(60) Provisional application No. 60/285,228, filed on Apr. 23, 2001.

(51) Int. Cl.[7] .............................................. G09F 9/00
(52) U.S. Cl. ...................... 62/125; 340/585; 206/459.1; 368/109
(58) Field of Search .......................... 62/125, 126, 127, 62/129, 130; 368/107, 108, 109; 340/585; 116/307, 308, 205; 283/55; 206/459.1

(56) References Cited

U.S. PATENT DOCUMENTS

| | | |
|---|---|---|
| D125,764 S | 3/1941 | Graesser et al. |
| D260,375 S | 8/1981 | Kane et al. |
| 4,285,697 A | 8/1981 | Neary .................... 23/230 LC |
| D271,182 S | 11/1983 | Iorio |
| D303,771 S | 10/1989 | Chan |
| 5,229,981 A | 7/1993 | Maschi ....................... 368/111 |
| 5,243,579 A | 9/1993 | Potthof ....................... 368/107 |
| 5,335,509 A | 8/1994 | Namisniak et al. ........... 62/125 |
| 5,487,276 A | 1/1996 | Namisniak et al. ........... 62/125 |
| 5,711,160 A | 1/1998 | Namisniak et al. ........... 62/125 |
| 5,802,015 A | 9/1998 | Rothschild et al. ........... 368/10 |
| D401,526 S | 11/1998 | Stunder |
| 5,892,734 A | 4/1999 | Flores et al. .................. 368/80 |
| D417,167 S | 11/1999 | Stunder |

FOREIGN PATENT DOCUMENTS

| | | | |
|---|---|---|---|
| GB | 2 042 775 A | 9/1980 | |
| GB | 2 145 699 A | 4/1985 | |
| JP | 5-149670 | * 6/1993 | .................. 62/125 |

* cited by examiner

Primary Examiner—Harry B. Tanner
(74) Attorney, Agent, or Firm—Richard C. Litman

(57) ABSTRACT

A food storage monitoring system device comprising a battery powered digital timer device having an LCD digital readout describing the elapsed days and hours per day, and a reset button to reset the timer. A magnet is permanently attached to the timer device, and removably attached to a ferromagnetic catch having a double sided adhesive tape attached to one face for attaching the catch to a food storage container. A set of devices can be stored on a refrigerator or freezer door. The catch is adhesively attached to a food storage container, and the timer device is magnetically attached to the catch with the timer device started. Upon retrieving the food container and emptying its contents, the timer device and the first magnet portion is returned to the refrigerator or freezer door, and the empty container and the attached catch can be washed in a dishwasher.

17 Claims, 4 Drawing Sheets

DEVICE TO RECORD AGE OF FOOD

CROSS-REFERENCE TO RELATED APPLICATION

This application claims the benefit of U.S. Provisional Patent Application Serial No. 60/285,228, filed Apr. 23, 2001.

BACKGROUND OF THE INVENTION

1. Field of the Invention

The present invention relates generally to food monitoring systems. More specifically, the invention is a kit containing a group of battery energized food timer devices having a reset function, an instruction sheet, a list of food items with their perishable refrigerated limits, clips, hooks, and double-stick tape. Each device has a count up timer function and is attached permanently to a magnetic disk, attachable to a food container by a steel disk having an adhesive peel backing.

2. Description of Related Art

The related art of interest describes various food monitoring systems, but none discloses the present invention. There is a need for a kit which supplies a simple and economical dating system for stored food. The related art is discussed in the order of perceived relevance to the present invention.

U.S. Pat. No. 5,711,160 issued on Jan. 27, 1998, which is a continuation-in-part of U.S. Pat. No. 5,487,276 issued on Jan. 30, 1996, and which is a continuation-in-part of U.S. Pat. No. 5,335,509 issued on Aug. 9, 1994, to Dianna Namisniak et al. describes a food storage tracking system placed on a refrigerator door comprising a rectangular base unit with a magnetic back including an electronic recording microprocessor, a column of preprinted magnetic tabs identifying foods and lifetime, a column timing display in days, a column of start buttons, a column of stop buttons, and a dry erasable pen in a pen holder. The device is distinguishable for requiring preprinted magnetic tabs for identifying each food, and start and stop/reset buttons for recording days of storage only on the refrigerator door.

U.S. Design Pat. No. 401,526 issued on Nov. 24, 1998, and U.S. Design Pat. No. 417,167 issued on Nov. 30, 1999, to Bernadette Stunder describes an adhesive-backed food freshness indicator disk device having a disk with an index mark and rotatable indices for dates and months. The device is distinguishable for its different distinct structure requiring manual manipulation and presumably renewal of the adhesive backing.

U.S. Pat. No. 5,243,579 issued on Sep. 7, 1993, to Erwin Potthof describes an electronic apparatus for monitoring the remaining storage period of frozen foods comprising a module incorporating an electro-optical display, a control electronics with a memory or data storage, input elements for entering the type of food and remaining storage period, a switch element for initiating data storage, an identification number of the food, and indication of an expired storage period for a food by generating a warning signal. The apparatus is distinguishable for its singular directory structure which is not attached to any specific food container.

U.S. Pat. No. 5,892,734 issued on Apr. 6, 1999, to Amal M. Flores et al. describes a magnetic-backed time-indicating device comprising a clock movement with hour and minute hands mounted on a ferrous clock face by a magnet. The device is distinguishable for its clock function and structure.

U.S. Pat. No. 4,285,697 issued on Aug. 25, 1981, to Michael P. Neary describes a food spoilage indicator device comprising a liquid crystal such as a cholesteryl chloride disposed in a carrier of plastic tape, wherein at least one portion of which is semi-permeable to gases generated in food spoilage. The device is distinguishable for its chemically reactive spoilage indicator.

U.S. Design Pat. No. 271,182 issued on Nov. 1, 1983, to Anthony J. Iorio describes an ornamental design of an electronic timer device having an inclined display screen and 12 input buttons on a circular base. The device is distinguishable for its unique timer structure.

U.S. Design Pat. No. 303,771 issued on Oct. 3, 1989, to Raymond Chan describes an ornamental timer device having an oblong shaped body containing a liquid crystal display indicator for hours and minutes, and push-buttons for minutes, seconds, and start/stop. The device is distinguishable for its timer structure.

U.S. Design Pat. No. 125,764 issued on Mar. 11, 1941, to Carl H. Graesser et al. describes a design for a gauge dial comprising a circular face with numerical indices from zero to 15. The device is distinguishable for its limited dial structure.

U.S. Design Pat. No. 260,375 issued on Aug. 25, 1981, to Earl B. Kane et al. describes an ornamental timer device comprising a rectangular body with a timer face indicating a scale from 5 to 55 and a rotatable pointer. Two other switch buttons are present. The timer device is distinguishable for its distinctive structure.

U.S. Pat. No. 5,229,981 issued on Jul. 20, 1993, to Louis P. Maschi describes a digital multi-event timer device for use in childbirth comprising a rectangular module containing an electronic time base for generating clock signals, an electronic counter for generating interval signals, and a liquid crystal display representing time in hours, minutes and seconds in actual time and elapsed time. The device is distinguishable for its multiple electronic time bases.

U.S. Pat. No. 5,802,015 issued on Sep. 1, 1998, to Alan W. Rothschild et al. describes a rectangular electronic timing label device for indicating the expiration of a time period attachable to a medicine bottle and the like. The label is attached by either an adhesive, a magnet, a band, hook and loop fasteners, hooks, clips, static cling film, or an electrotet film. The device contains a programming conductor port, a pulse generator, a binary counter, a liquid crystal display, a printed circuit board, and a battery. The device is distinguishable for its programmable requirement by a separate personal computer.

U.K. Patent Application No. 2 042 775 A published on Sep. 24, 1980, for Moriyoshi Kurosawa describes a stop-watch or chronograph comprising a module containing on its face a thermal printing head and paper, two liquid display screens for displaying lap times and the time of day (clock), and two power switches. On one side five push buttons for starting, stopping, etc. are located. A battery and electric drive circuitry are included. The lap counting stop-watch is distinguishable for its required numerous push button controls and its thermal printing head and paper.

U.K. Patent Application No. 2 145 699 A published on Apr. 3, 1985, for Peter R. Dearing-Lambert et al. describes a box device for monitoring the use of medicines comprising a lockable container for medicines having a lid controlled by a solenoid which is automatically controlled to unlock when the circuit signals based on a clock to activate an audible or visible signal. The box device is distinguishable for its multiple controls.

None of the above inventions and patents, taken either singly or in combination, is seen to describe the instant invention as claimed.

SUMMARY OF THE INVENTION

The present invention is directed to a kit containing a set of circular food timer devices, wherein each device has a count up timer energized by a lithium battery to indicate the number of days and hours on its face. A recessed timer reset button is also on the face. A magnet is permanently attached to the timer device. A steel disk commensurate in size to the magnet has a double faced adhesive tape with a peelable cover sheet. The devices without the steel disks are stored on the refrigerator or freezer door. When a food container is to be refrigerated, the device's timer is started and placed on the steel disk (with adhesive cover removed) which has been placed on the food containing container. When the container is emptied, the timer portion with the magnet is placed back on the refrigerator door and the empty container with the steel disk on the cover can be washed in a dishwasher. In this manner, the container can be reused with the steel disk attached to its cover to be combined with the timer and magnet for reuse. The convenient kit includes a set of the timer devices, clips, hooks, a list of foods and their refrigerated lifetimes, and an instruction sheet for utilizing the timer device system. The clips and hooks are conveniently utilized for tagging containers with handles and the like.

Accordingly, it is a principal object of the invention to provide a kit for keeping track of refrigerated foods.

It is another object of the invention to provide a timer device in the kit for displaying the elapsed time in days and hours during refrigeration.

It is a further object of the invention to provide a timer device having a reset ability.

Still another object of the invention is to provide a timer having a magnetic base for storage on a refrigerator door when not in use.

Yet another object of the invention is to provide a steel base with an adhesive backing for attaching the timer device to a food container.

Yet still another object of the invention is to further provide in the kit, disk clips, hooks, an instruction sheet and a list of food items with their perishable dates.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
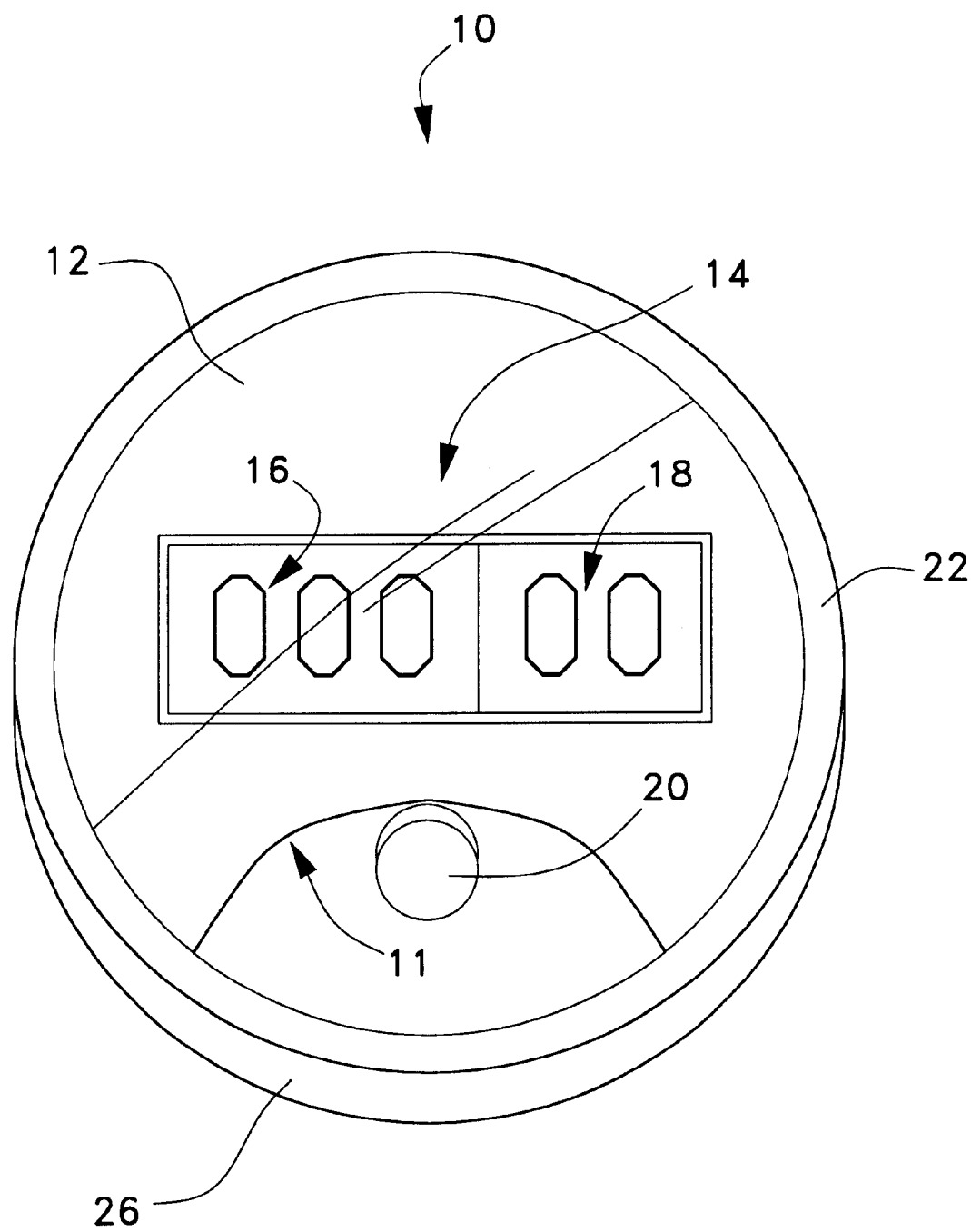
FIG. 1 is a perspective view of a watch device to record the age of food according to the present invention.
Figure 2:
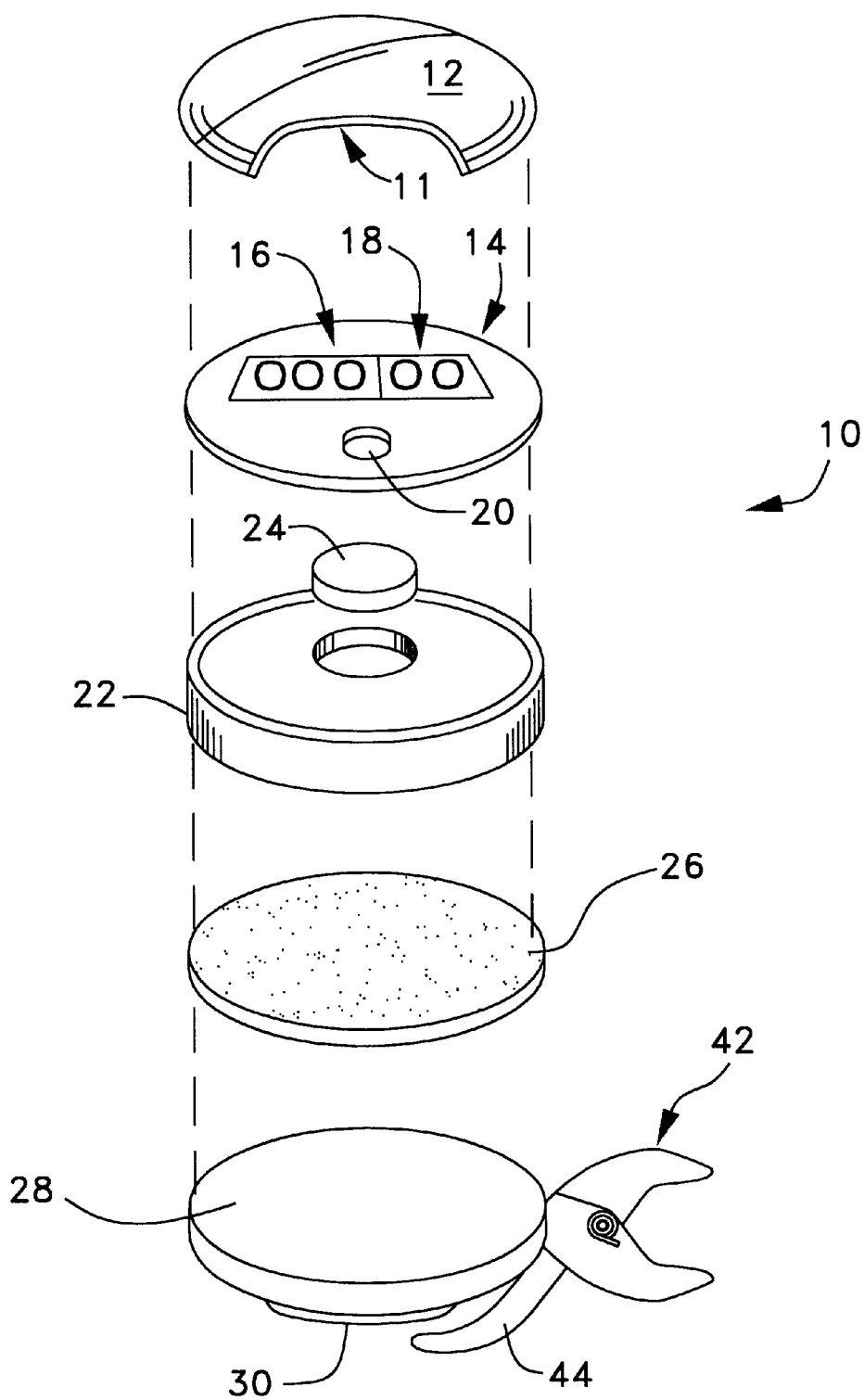
FIG. 2 is an exploded view of the watch device including a lithium battery and a microcomputer inside the watch face portion.

The present invention, shown in FIGS. 1 and 2, is directed to a food storage monitoring device for recording the age of food comprising a timer device 10 having a transparent crystal cover 12 with a partial cutaway portion 11 covering a liquid crystal display (LCD) face element 14 having a digital readout of elapsed days 16 with three digits on the left, elapsed hours 18 with two digits on the right, and a slightly recessed reset button 20. It is important that the reset button 20 is recessed to avoid an accidental reset to zero. A circular base portion 22 contains conventional electronic timer circuitry driven by a lithium battery 24 installed in a depression in the base portion 22 for counting the time which has elapsed after pressing the reset button in days and hours, and for driving the LCD display 14.

Figure 4:
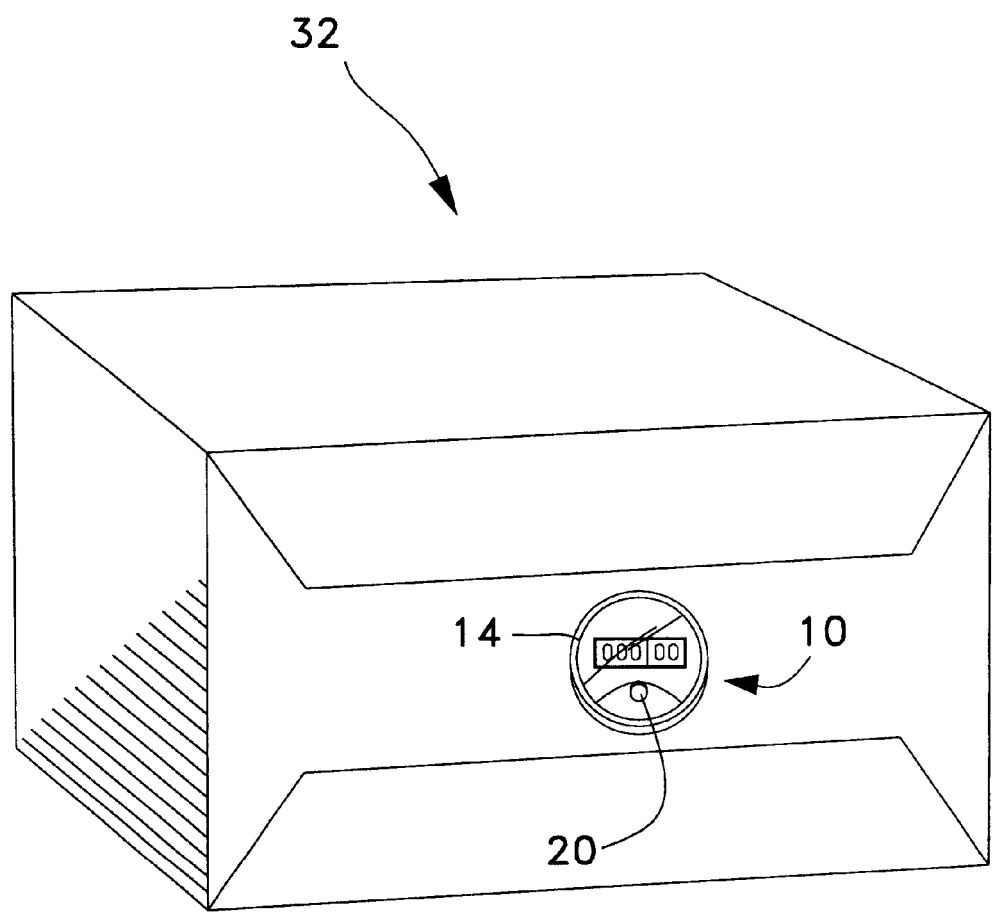
FIG. 4 is a perspective view of a food container with the watch device adhered to a surface.

A magnetic base 26 commensurate in size to the timer device 10 is attached to a rear face of the timer device. A catch 28 made from ferromagnetic material, preferably a thin, flat, steel disk, has one exposed face with a surface area which is preferably commensurate in size to the magnetic base 26 so that the timer device 10 is removably attachable to the base 28 by magnetic attraction. Alternatively, the catch 28 may be a second magnet of opposite polarity. A conventional piece of double-sided adhesive coated tape 30 (shown in FIG. 2) is attached to the opposite face of the catch 28, and has a non-adhesive cover for the adhesive tape which is peeled off in order to attach the catch 28 to a food container 32, as illustrated in FIG. 4. Alternatively, a spring-loaded clip 42 with a lever 44 can be permanently attached to the catch 28 for attaching the catch 28 to a food container for refrigeration.

The timer device 10 may be marketed in kit form, the kit providing a set of timer devices 10, an instruction sheet (not shown) for operating the device, a list of foods (not shown) with their recommended safe storage time, and a roll of double-sided adhesive tape, the levered clip 42, hooks, or other means for attaching the catch 28 to a food storage container.

Figure 3:
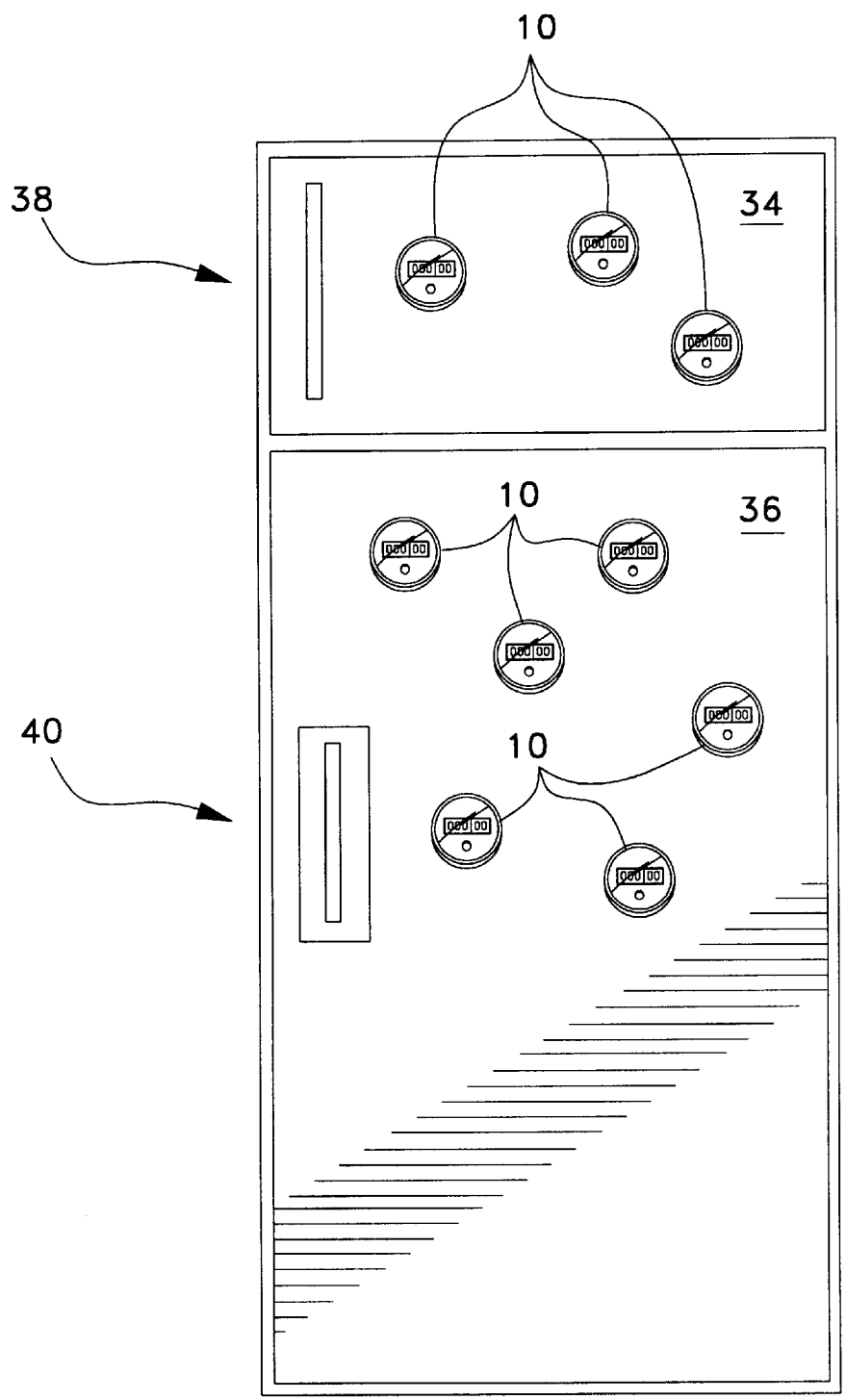
FIG. 3 is a front elevational view of a plurality of watch devices on a refrigerator door.

When the food container 32 is emptied of its contents, the timer device 10 can be stored on the doors 34 and 36 of a freezer compartment 38 or a refrigerator compartment 40, respectively, as illustrated in FIG. 3, by virtue of the magnetic base 26. The steel disk adhesively attached to a food container 32 can be washed in a dishwasher and the like and reused together with the container.

The advantages of using this system is manifold. There would be far less question as to which foods are safe for consumption. The system would reduce the risk of food poisoning from spoiled food. There is an economic saving for users who previously did not save leftover food. The cleaning of the refrigerator or freezer would be minimized in the home, institutions and industry by utilizing this dating system with reusable devices.

It is to be understood that the present invention is not limited to the sole embodiment described above, but encompasses any and all embodiments within the scope of the following claims.

We claim:

1. A food storage monitoring device for recording the age of food in storage, comprising:
 a timer device comprising an electronic timer having a front face and a rear face;
 a magnetic base attached to the rear face of the timer device;
 a catch, the magnetic base being removably secured to the catch by magnetic attraction; and
 means for attaching the catch to a food container;
 whereby the catch is attachable to a food storage container, the timer being started in order to record elapsed food storage time.

2. The food storage monitoring device according to claim 1, wherein the means for attaching is a spring-loaded clip with a lever, the clip being affixed to the catch.

3. The food storage monitoring device according to claim 1, wherein the catch is a flat catch made of ferromagnetic material.

4. The food storage monitoring device according to claim 1, wherein the timer device further comprises a digital display on the front face of the device capable of displaying elapsed days and hours.

5. The food storage monitoring device according to claim 4, wherein said digital display comprises a liquid crystal display.

6. The food storage monitoring device according to claim 1, wherein the timer device further comprises a reset button for resetting the timer, the reset button being disposed on the front face of said electronic timer.

7. The food storage monitoring device according to claim 1, wherein said catch comprises a flat steel disk.

8. The food storage monitoring device according to claim 1, wherein the device is washable after use for reuse.

9. The food storage monitoring device according to claim 1, wherein the means for attaching comprises double sided adhesive tape, the adhesive tape having a first side adhesively attached to said catch and a second side adhesively attachable to a food storage container.

10. A kit for recording the age of food in storage, comprising:

an instruction sheet for operating a timer device;

a list of foods with recommended safe storage times;

a roll of double-sided adhesive tape;

a plurality of timer devices, each of the timer devices comprising an electronic timer having a front face and a rear face;

a magnetic base attached to the rear face of each timer device; and a plurality of catches, each of the catches being removably secured to the timer devices by magnetic attraction to the magnetic base;

means for attaching the catches to a food storage container;

whereby each of the catches is attachable to a food storage container, the timer being started in order to record elapsed food storage time.

11. The food storage monitoring device according to claim 10, wherein the means for attaching comprises a spring-loaded clip with a lever, the clip being affixed to the catch.

12. The food storage monitoring device according to claim 10, wherein each catch is a flat catch made of ferromagnetic material.

13. The food storage monitoring device according to claim 10, wherein each said electronic timer further comprises a liquid crystal display disposed on the front face of said electronic timer.

14. The food storage monitoring device according to claim 10, wherein each said electronic timer further comprises a reset button for resetting said timer, the reset button being disposed on the front face of said electronic timer.

15. The food storage monitoring device according to claim 10, wherein each said catch comprises a flat steel disk.

16. The food storage monitoring device according to claim 10, wherein the device is washable after use for reuse.

17. The food storage monitoring device according to claim 10, wherein said means for attaching comprises double sided adhesive tape, the adhesive tape having a first side adhesively attached to said catch and a second side adhesively attachable to a food storage container.

* * * * *